United States Patent [19]

Appelgren et al.

[11] Patent Number: 4,562,061
[45] Date of Patent: Dec. 31, 1985

[54] PHARMACEUTICAL PREPARATION

[75] Inventors: Curt H. Appelgren, Kungsbacka; Conny B. Bogentoft, Kållered; Gunnar H. Ekenved, Kungsbacka, all of Sweden

[73] Assignee: Aktiebolaget Hassle, Sweden

[21] Appl. No.: 716,522

[22] Filed: Mar. 27, 1985

Related U.S. Application Data

[63] Continuation of Ser. No. 563,542, Dec. 20, 1983, abandoned, which is a continuation of Ser. No. 369,934, Apr. 19, 1982, abandoned.

[30] Foreign Application Priority Data

Apr. 27, 1981 [SE] Sweden ................... 8102637

[51] Int. Cl.$^4$ .......................... A61K 9/32; A61K 9/36
[52] U.S. Cl. .......................................... 424/32; 424/35
[58] Field of Search .............................. 424/32, 33, 35

[56] References Cited

U.S. PATENT DOCUMENTS

| | | |
|---|---|---|
| 2,702,264 | 2/1955 | Kläul ..................... 424/33 |
| 3,275,518 | 9/1966 | Endicott et al. ............... 424/32 |
| 3,520,970 | 7/1970 | Lehmann et al. .............. 424/25 |
| 3,775,537 | 11/1973 | Lehmann et al. .............. 424/81 |
| 3,954,959 | 5/1976 | Pedersen ..................... 424/21 |
| 4,060,598 | 11/1977 | Groppenbacher et al. ......... 424/32 |
| 4,083,949 | 4/1978 | Benedikt ..................... 424/19 |
| 4,198,402 | 4/1980 | Ezer et al. .................. 424/232 |
| 4,218,433 | 8/1980 | Kooichi et al. ............... 424/21 |
| 4,223,008 | 9/1980 | Gregory ...................... 424/35 |
| 4,261,971 | 4/1981 | Appelgren et al. ............. 424/21 |
| 4,263,273 | 4/1981 | Appelgren et al. ............. 424/21 |
| 4,341,759 | 7/1982 | Bogentoft et al. ............. 424/21 |
| 4,367,217 | 1/1983 | Gruber et al. ................ 424/32 |

FOREIGN PATENT DOCUMENTS

| | | |
|---|---|---|
| 1792447 | 11/1971 | Fed. Rep. of Germany . |
| 24k8622 | 11/1979 | France . |
| 2038181 | 7/1980 | United Kingdom . |
| 2966973 | 7/1981 | United Kingdom . |

OTHER PUBLICATIONS

Delporte et al, Chem. Abstr. 85, #83190r, (1976) of J. Pharm. Belg., (1976) 31(3): 263–276, Effect of the Formulation of Enterosoluble Preparations on the Drug Bioavailability, Part 4, Effect of the pH of Dissolution of the Applied Enteric Polymer on . . . Acetylsalicylic Acid Tablets.

Cadorniga et al, Chem. Abstr. 86, #161217s, (1977) of Cienc. Ind. Farm., (1976), 8(12): 362–8, Release Rate of Acetylsalicylic Acid (AAS) Contained in Microcapsules of Methacrylic Acid Copolymers.

J. Pharm. Belg., 1976, 31, 2, pp. 150–168, J. P. Delporte.

J. Pharm. Belg., 1975, 30, 2, pp. 99–113, J. P. Delporte et al.

J. Pharm. Belg., 1976, 31, 1, pp. 38–50, J. P. Delporte et al.

Primary Examiner—Shep K. Rose
Attorney, Agent, or Firm—Brumbaugh, Graves, Donohue & Raymond

[57] ABSTRACT

According to the present invention an oral pharmaceutical preparation of acetylsalicylic acid is provided which consists of cores containing acetylsalicylic acid as pharmaceutically active component, which cores are coated with a polymer membrane to the formation of coated granules. The preparation is characterized in that the polymer membrane comprises at least one polymer selected from the group consisting of cellulose acetate phtalate and methyl esterified methacrylic acid polymers having a degree of esterification of 45–55%, whereby the amount of such polymer forms 60–45% of the weight of the membrane, and at least one methyl esterified methacrylic acid polymer having a degree of esterification of 65–75% and forming 45–25% of the weight of the membrane, and a plasticizer selected from fatty alcohols and fatty acids forming 4–12% of the weight of the membrane, whereby the membrane represents 5–12 weight % of the composition. With this composition a reduced effect on the gastric mucosa as compared with previously known preparations but retaining good absorbtion properties and a controlled release.

2 Claims, No Drawings

PHARMACEUTICAL PREPARATION

This application is a continuation of application Ser. No. 563,542, filed on Dec. 20, 1983 which is a continuation of application Ser. No. 369,934, filed Apr. 19, 1982, both abandoned.

TECHNICAL FIELD

The present invention is related to a new pharmaceutical preparation for the administration of acetylsalicylic acid, to a method for the manufacture of such a preparation and to a method for treatment of rheumatic and inflammatory diseases based on such a preparation.

One object of the invention is to make available an improved acetylsalicylic acid preparation, which gives a reduced effect on the gastric mucosa in comparison with previously known preparations but retaining good absorption properties and a controlled release, which results in an even plasma concentration of acetylsalicylic acid.

STATE OF THE ART

Acetylsalicylic acid (ASA) presents a basic therapy in the treatment of rheumatic and degenerative diseases of the joints. A good anti-inflammatory effect is considered to be correlated to plasma levels between 1.1 and 2.2 mmoles/1 determined as total salicylate. Close above these levels one finds the range for "salicylism". An even plasma concentration during the day is expected to give an even effect, even if this is difficult to determine. An even plasma level is also considered to result in a lower probability for side-effects. A slow absorption results e.g. in a lower frequency of hearing disturbances because a small variation of the plasma level at high concentrations may effect the hearing.

A common side-effect of ASA is bleeding and other effects on the ventricular mucosa. These problems are amplified at prolonged treatment at high dosages, as is common in the treatment of rheumatism.

It is well known that gastric juice resistant coating can reduce bleeding from the ventricular mucosa. It seems however with some patients to be difficult to completely avoid lesions in this way. One possible cause can be that the contents from the small intestine after dissolving the gastric juice resistant coating causes erosion lesions because of reflux up to the ventricle. Bile salts together with acetylsalicylic acid seem in fact to play a not insignificant role in the pathogenesis of gastritis. Many patients with gastritis and bleedings caused by ASA have reflux of bile salts and contents of the small intestine.

The risk of ventricle damages ought therefore to be reduced considerably if the release of ASA occurs more distally in the small intestine.

DISCLOSURE OF THE INVENTION

According to the present invention an oral pharmaceutical preparation of acetylsalicylic acid is provided which consists of cores containing acetylsalicylic acid as pharmaceutically active component, which cores are coated with a polymer membrane to the formation of coated granules, characterized in that the polymer membrane comprises at least one polymer selected from the group consisting of cellulose acetate phtalate and methyl esterified methacrylic acid polymers having a degree of esterification of 45-55%, whereby the amount of such polymer forms 60-45% of the weight of the membrane, and at least one methyl esterified methacrylic acid polymer having a degree of esterification of 65-75% and forming 45-25% of the weight of the membrane, and a plasticizer selected from fatty alcohols and fatty acids both having a straight saturated chain containing 12 to 20 carbon atoms forming 4-12% of the weight of the membrane, whereby the membrane represents 5-12 weight-% of the composition. With this composition the above mentioned objects can be met. Preferred preparations are those wherein the components of the coating have been selected so that the released amount of ASA after 2 hours exposition in vitro at the given pH meets the following criteria

| pH 1 | max 6% |
|---|---|
| pH 5.7 | max 15% |
| pH 6.5 | max 90% |
| pH 7.0 | min 70% |

As examples of methyl esterified methacrylic acid polymers with 45-55% esterification, which may form the first-mentioned component of the coating, can be cited Eudragit L ® (degree of esterification 53 mole-%) and MPM-05 (degree of esterification 52 weight-%). As examples of methyl esterified methacrylic acid polymers with a degree of esterification of 65-75%, which form the second component of the coating, can be mentioned Eudragit S ® (degree of esterification 72 mole-%) and MPM-06 (degree of esterification about 70 mole-%). The third above-mentioned component of the coating is a plasticizer preferably selected among cetanol and stearic acid.

The granules prepared according to the invention are suitably of a size 0.1 to 3 mm.

The composition according to the invention can be administered as granulate, be compressed to tablets or preferably be contained in capsules, e.g. hard gelatine capsules, containing a therapeutically effective amount of the composition.

A process for the manufacture of a composition according to the above presents a further aspect of the invention. The method comprises spraying of acetylsalicylic acid granules with a solution containing the three above mentioned components of the coating, preferably in an organic solvent such as ethanol, isopropyl alcohol and/or methylene chloride. The spraying can be carried out in a coating pan, but preferably in a fluidized bed.

The composition according to the invention is particularly advantageous in the treatment of rheumatic and/or inflammatory diseases, and a method for the treatment of such conditions represents a further aspect of the invention.

WORKING EXAMPLES 500 g ASA-granules (ASA-gran 7017, Monsanto) of a particle size 0.5-1.2 mm were coated by spraying with a solution of the in Table 1 mentioned composition i an Aeromatic Strea 1 fluidized bed equipment.

Release tests were carried out with all coated granules in a phosphate buffer pH=6.5 and in some tests also in artificial gastric juice. The analyses results are listed in table 2.

Analysis method

Glass beaker: 600 ml with rotating basket, 150 r/min.

Medium: 500 ml artificial gastric juice and phosphate buffer pH=6.5 μ=0.24
Temp.: 37° C.±0.1° C.

Granules with a coating according to table 3 were manufactured in the same way. Release tests carried out as above are reported in table 4. As comparison in table 4 the results or analysis of a previously in Sweden marketed granular acetylsalicylic acid composition with a gastric juice resistant coating (Ref.) are included. Table 5 contains the results of analysis after 2 hours release at pH 5.7 and 7.0 for some preparations.

TABLE 1

Coating solutions

| Example no | CAP[1] g | E:S[2] g | Cetanol g | Stearic acid g | Methylene chloride g | Isopropanol g | Coating time min |
|---|---|---|---|---|---|---|---|
| 1 | 18 | 16 | 4.6 | | 500 | 300 | |
| 2 | 22 | 14 | 2.6 | | 500 | 300 | 17 |
| 3 | 24 | 10 | | 4.6 | 513 | 275 | |
| 4 | 16.5 | 10.5 | 2.0 | | 375 | 225 | 13 |
| 5 | 33 | 21 | 3.9 | | 750 | 450 | 26 |

[1]Cellulose acetate phtalate
[2]Eudragit S

TABLE 2

Results from release tests with coated ASA-granules

% ASA released in

| | gastric juice after | | phosphate buffer, pH = 6.5, after | | | | | |
|---|---|---|---|---|---|---|---|---|
| Example | 2 | 4 h | 0.5 | 1 | 1.5 | 2 | 2.5 | 3 | 4 h |
| 1 | | | | 14 | 31 | 51 | 70 | 87 | 95 | 102 |
| 2 | | | | 22 | 45 | 69 | 90 | 100 | 103 | 104 |
| 3 | 2 | 4 | 39 | 70 | 89 | 98 | 101 | 101 | 102 |

TABLE 3

Coating solutions

| Example No. | E:L[1] g | E:S[2] g | Cetanol g | Stearic acid g | Solvent type | amount, g | Coating time min |
|---|---|---|---|---|---|---|---|
| 6 | 22 | 12 | 4.6 | | abs EtOH | 600 | 30 |
| 7 | 24 | 12 | | 2.6 | 95% EtOH | 600 | 29 |
| 8 | 18 | 18 | | 2.6 | MeCl$_2$ + IPA | 500 + 300 | 17 |
| 9 | 20 | 16 | | 2.6 | MeCl$_2$ + IPA | 500 + 300 | 20 |
| 10 | 20 | 16 | | 2.6 | MeCl$_2$ + IPA | 500 + 300 | 24 |

[1]Eudragit L
[2]Eudragit S

TABLE 4

Results of release tests with coated ASA-granules

% ASA released in

| Example No. | gastric juice after | | phosphate buffer pH = 6.5 after | | | | | | |
|---|---|---|---|---|---|---|---|---|---|
| | 2 | 4 h | 0.5 | 1 | 1.5 | 2 | 2.5 | 3 | 4 h |
| 6 | 1 | 2 | 16 | 35 | 56 | 75 | 87 | 96 | 100 |
| 7 | <1 | 2 | 40 | 81 | 100 | 100 | | | |
| 8 | | | 18 | 48 | 75 | 90 | 97 | 100 | 101 |
| 9 | <1 | | 19 | 40 | 65 | 82 | 94 | 100 | 102 |
| 10 | <1 | | 21 | 45 | 69 | 89 | 100 | 102 | 103 |
| Ref. | 2-3 | 4-6 | 90-100 | | | | | | |

TABLE 5

Results of release tests with coated ASA-granules.

| Example No. | % ASA released after 2 h at | |
|---|---|---|
| | pH 5.7 | pH 7.0 |
| 2 | 9 | 100 |
| 4 | 15 | 100 |
| 5 | 3 | 100 |
| 9 | 7 | 100 |
| Ref. | 60 | 100 |

Gastroscopic studies

In this test such changes in the mucosa which can be observed with the aid of gastroscopy after a period of treatment covering 3 days with a daily dose of 3×1 g were studied. Test persons were 9 healthy volunteers, who had not earlier shown intolerance to ASA administration. A preparation according to the invention (Example 2) and the above mentioned previously marketed preparation were studied and compared. The preparations were tested with an interval of 3 weeks. Gastroscopy was carried out after each period of treatment. The gastroscopic evaluation was made blind. The test persons were fasting from 10 o'clock p.m. the night before the test. The status of the ventricular mucosa was classified according to the following:

0 = normal mucosa
+ = singular light erosions
+ + = multiple pronounced erosions

Results

See table 6.

TABLE 6

Results of gastroscopic investigation

| Test person | Example 2 Erosions | Status | Ref. Erosions | Status | Comparison |
|---|---|---|---|---|---|
| BH | — | 0 | 3 small with coagulums | + | (S) |
| AS | — | 0 | — | 0 | (E) |
| IH | — | 0 | several small in antrum and corpus | + + | (S) |
| WS | 3 positive very small | + | 3 small | + | (E) |
| RB | several | + + | 1 prepylorically 2 in antrum | + | (I) |

TABLE 6-continued

| Test person | Results of gastroscopic investigation | | | | Comparison |
|---|---|---|---|---|---|
| | Example 2 | | Ref. | | |
| | Erosions | Status | Erosions | Status | |
| TOB | — | 0 | several with coagulums | ++ | (S) |
| KJ | more than 5 | ++ | plenty of large and small with coagulums | ++ | (S) |
| RI | — | 0 | few small, some with coagulums | ++ | (S) |
| KN | at least 6 | ++ | several prepylorically, a couple of small in antrum and corpus | ++ | (E) |

S = The preparation according to the invention superior
L = Equal result
I = The preparation according to the invention inferior
The best preparation: Acc. to the invention 5 test persons
Ref. 1 test persons
Equal results 3 test persons
Ξ9 test persons Conclusion The results show that the composition according to Example 2 results in fewer erosions in 5 of the 9 studied individuals. Only in one test person has the reference preparation been evaluated to be somewhat better. The results thus show that the invention makes available a preparation which when used clinically on humans is an improvement.

Best mode of carrying out the invention

The best mode to carry out the invention is represented in Example 2.

We claim:

1. An oral pharmaceutical preparation containing coated acetylsalicylic acid granules (ASA), said granules being coated with a polymeric coating which releases about 70 to 90% of the ASA after 2 hours at a pH of 6.5 to 7 wherein said coating is 5 to 12% by weight of the preparation and said coating comprises 60 to 45% by weight of the membrane of at least one polymer selected from the group consisting of cellulose acetate phtalate and methyl esterified methacrylic acid polymers having 45 to 55% esterification; 45 to 25% by weight of the membrane of at least one methyl esterified methacrylic acid polymer having 65 to 75% esterification and 4 to 12% by weight of the membrane of a plasticizer selected from a group consisting of fatty alcohols and fatty acids both having a straight saturated carbon chain containing 12 to 20 carbon atoms.

2. A method for treating rheumatic and inflammatory diseases wherein a therapeutically effective amount of the preparation described in claim 1 is administered to a host in need of such treatment.

* * * * *

UNITED STATES PATENT AND TRADEMARK OFFICE
CERTIFICATE OF CORRECTION

PATENT NO. : 4,562,061

DATED : December 31, 1985

INVENTOR(S) : Curt H. Appelgren et al.

It is certified that error appears in the above-identified patent and that said Letters Patent is hereby corrected as shown below:

Title page:

Under "FOREIGN PATENT DOCUMENTS", "24k8622" should read -- 2419722 --; and "2966973" should read -- 2067073. Col. 3, line 7, "or" should read -- of --. Col. 5, line 11, "++" should appear under "Status" and "(S)" should appear under "Comparison".

Signed and Sealed this

Seventeenth Day of June 1986

[SEAL]

Attest:

DONALD J. QUIGG

Attesting Officer

Commissioner of Patents and Trademarks